United States Patent
Müller et al.

(10) Patent No.: US 6,841,385 B2
(45) Date of Patent: Jan. 11, 2005

(54) TRANSCRIPTION FACTOR E2F DNA-BINDING DOMAIN INHIBITOR PEPTIDES AND THEIR USE

(75) Inventors: Rolf Müller, Marburg (DE); Roland E. Kontermann, Marburg (DE); Silvia Montigiani, Siena (IT)

(73) Assignee: Topotarget UK Limited, Abingdon (GB)

( * ) Notice: Subject to any disclaimer, the term of this patent is extended or adjusted under 35 U.S.C. 154(b) by 50 days.

(21) Appl. No.: 09/912,414

(22) Filed: Jul. 26, 2001

(65) Prior Publication Data

US 2003/0013169 A1 Jan. 16, 2003

(30) Foreign Application Priority Data

Jan. 26, 1999 (GB) ............................................. 9901710

(51) Int. Cl.[7] ............................. C12N 5/02; C07K 7/00; C07K 14/00; C07K 14/435; C07K 19/00; A61K 39/00
(52) U.S. Cl. ........................ 435/375; 530/324; 530/325; 530/326; 530/327; 530/328; 530/329; 530/350; 424/185.1
(58) Field of Search ................................. 530/324, 325, 530/326, 327, 328, 329, 350; 435/375

(56) References Cited

U.S. PATENT DOCUMENTS 5,728,802 A * 3/1998 Barrett et al. ................ 530/324

FOREIGN PATENT DOCUMENTS

| EP | 0 963 999 | 12/1999 |
| JP | 06192290 A | * 7/1994 |
| WO | WO9418345 | * 8/1994 |
| WO | WO98/28334 | 7/1998 |
| WO | WO9945121 | * 9/1999 |

OTHER PUBLICATIONS

L R Bandhara et al.: "Apaptosis induced in mammalian cells by small peptides that functionally antagonize the Rb–regulated E2F transcription factor" Nature Biotechnology., vol. 15, No. 9, Sep. 1997, pp. 896–901, XP002061240 Nature Publishing., US.

File Medline, abstract 95059071 XP002137731 & M Xu et al.: "Cyclin A/CDK2 binds directly to E2F–1 and inhibits the DNA–binding activity of E"F–1/DP–1 by phosphorylation" Molecular and Cellular Biology., vol. 14, No. 12, Dec. 1994, pp. 8420–8431, American Society for Microbiology, Washington., US.

File Medline, abstract 92236563, 1992 XP002137732 & S M Stirdivant et al.: "Human papillomavirus type 16 E7 protein inhibits DNA binding by the retinoblastoma gene product" Molecular and Cellular Biology., vol. 12, No. 5, May 1992, pp. 1905–1914, American Society for Microbiology, Washington., US.

* cited by examiner

Primary Examiner—Terry McKelvey
(74) Attorney, Agent, or Firm—Nixon & Vanderhye P.C.

(57) ABSTRACT

The present invention provides peptides which bind to the DNA binding domain of transcription factor E2F, and inhibit cell cycle progression. Peptides include FWLRFT (SEQ ID NO:1); WVRWHF (SEQ ID NO:2); WHFIFW (SEQ ID NO:3); IWLSGLSRGVWVSFP (SEQ ID NO:4); and GSRILTFRSGSWYAS (SEQ ID NO:5) and derivatives based upon these sequences. Compositions and the use of the peptides in inhibiting cell cycle progression, such as in uncontrolled cell proliferation, are also provided.

16 Claims, 3 Drawing Sheets

TRANSCRIPTION FACTOR E2F DNA-BINDING DOMAIN INHIBITOR PEPTIDES AND THEIR USE

FIELD OF THE INVENTION

The present invention relates to polypeptides which act as inhibitors of E2F-DNA binding, and their use.

BACKGROUND TO THE INVENTION

The transcription factor E2F plays a predominant role in regulating the transition from G1 to S phase of the cell cycle (La Thangue (1994) Trends Biochem. 19, 108–114; Müller (1995) Trends Genetics 11, 173–178). E2F is a heterodimeric factor consisting of one component of the E2F family and one component of the DP family. Six members of the E2F family and two members of the DP family have been identified in humans. While all members of the E2F family can form heterodimers with both DP members, they show a preferential binding to the different members of the pocket protein family. E2F1–3 interact with pRB, while E2F4 binds preferentially p107 and 130 but also pRB, and E2F5 only p130. Differences between the E2F members exist also in binding of cyclin A/cdk2 complexes. Binding sites for these complexes are found only in E2F1–3 (Beijersbergen & Bernards (1996) Biochem. Biophys Acta 1287, 103–130)

DISCLOSURE OF THE INVENTION

Figure 1:
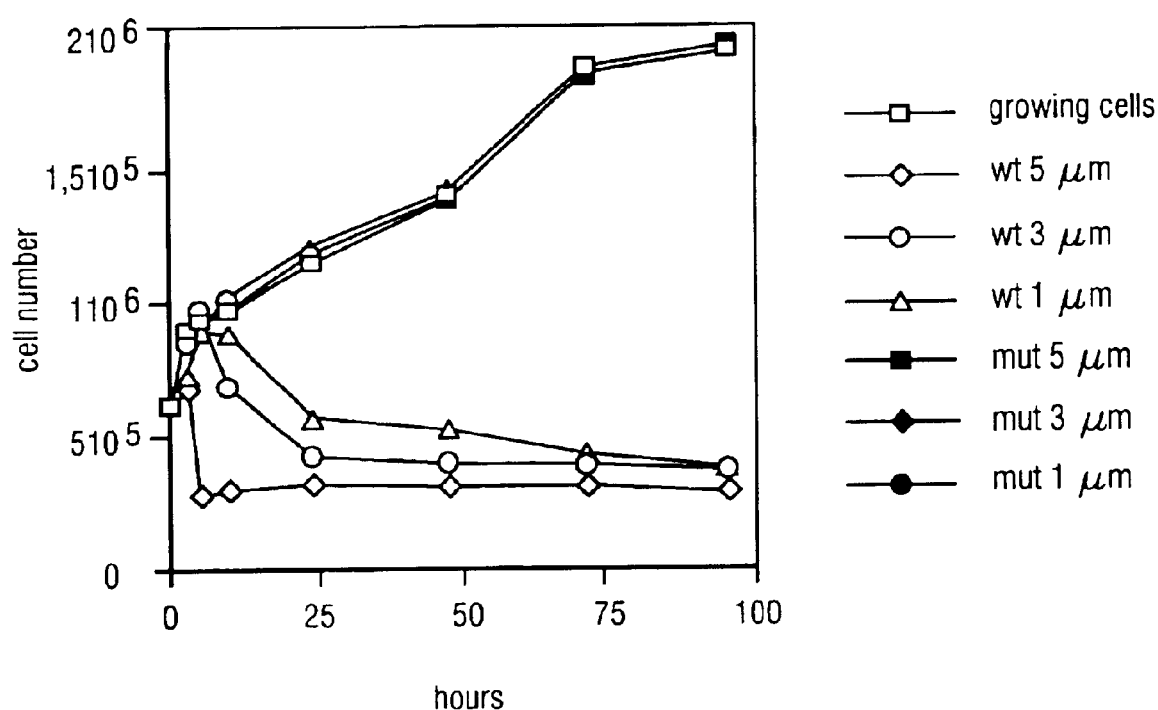
FIG. 1 shows a growth curve of HL60 cells treated with a peptide of the invention in a branched format (MAP-SEQ ID NO:2-TAT), indicated as (wt) at concentrations of 1, 3 and 5 μM and a control (MAP-SEQ ID NO:39-TAT) ("mut") at the same concentrations.
Figure 2A:
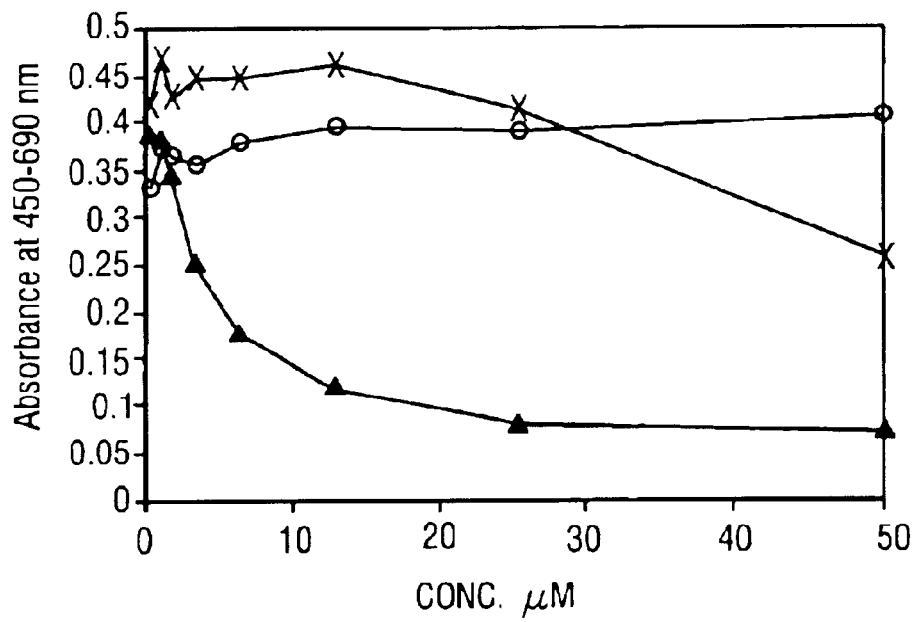
FIGS. 2A-D shows growth curves of four further cell lines (A—U2OS; B—HeLa; C—E2F4/ras; D—C33A) treated with the peptide (triangles) and control peptide (x) as for FIG. 1, at a variety of concentrations. Untreated controls are also shown (open circles).
Figure 2B:
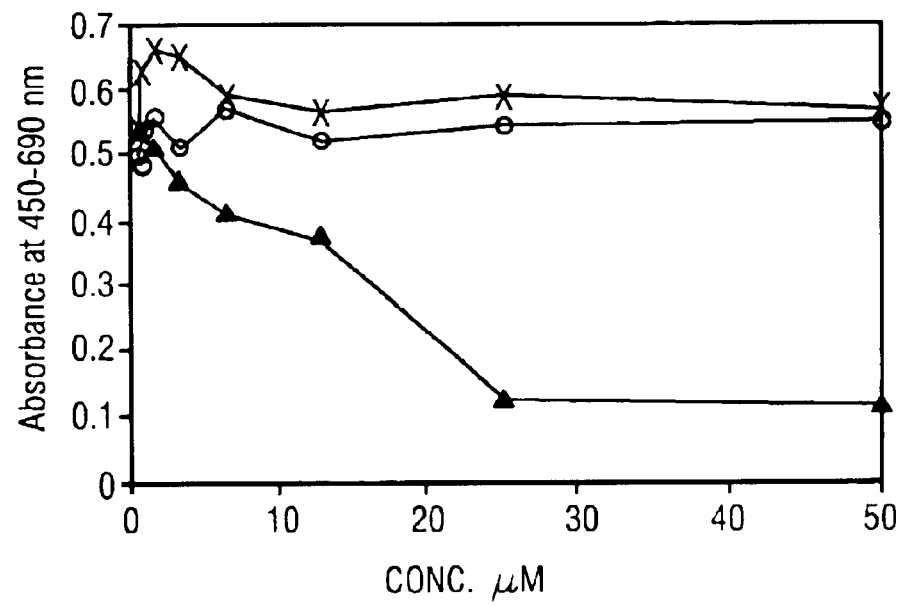
Figure 2C:
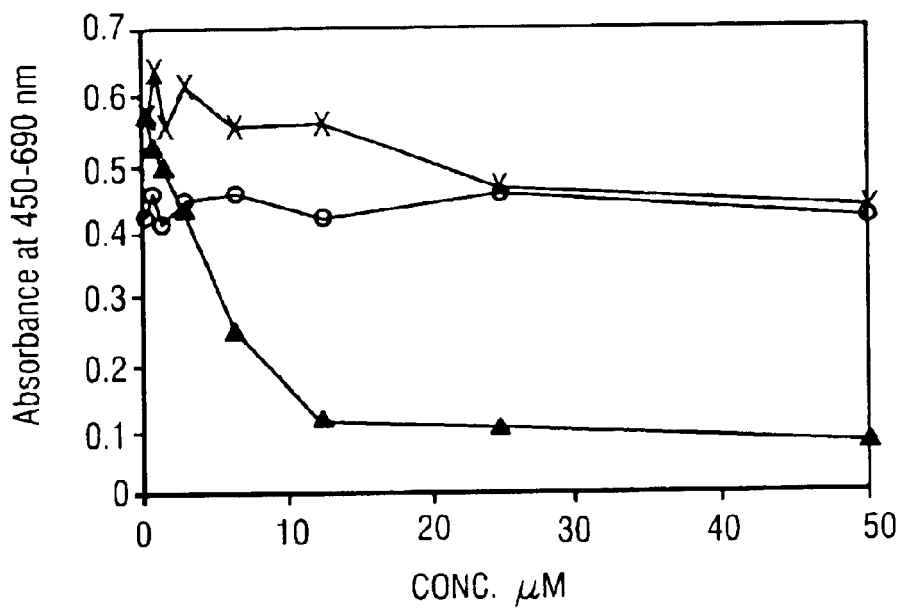
Figure 2D:
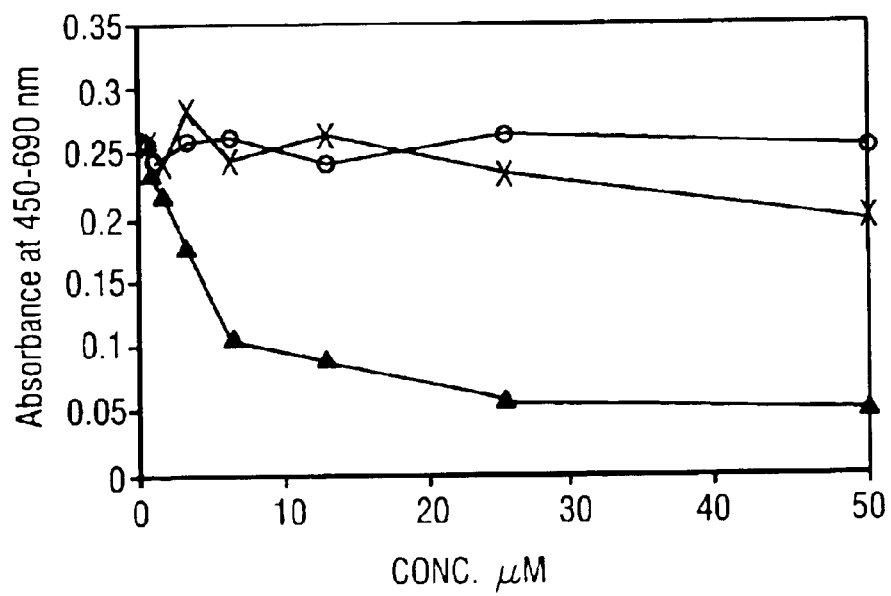

We have identified a number of peptides which are capable of binding to the DNA binding domain of E2F-1, and which inhibit the binding of E2F family members to DNA, thus inhibiting E2F function. Inhibition of E2F function by peptides of the invention was found to inhibit cell cycle progression and to induce apoptosis.

Accordingly, the present invention provides a polypeptide comprising a sequence selected from the group consisting of:

FWLRFT (SEQ ID NO:1);
WVRWHF (SEQ ID NO:2);
WHFIFW (SEQ ID NO:3);
IWLSGLSRGVWVSFP (SEQ ID NO:4); and
GSRILTFRSGSWYAS (SEQ ID NO:5).

or a fragment thereof capable of binding to an E2F DNA-binding site.

In a further aspect of the invention, there is provided a functional variant of the above polypeptide, which variant comprises from one to four, preferably from one to three, more preferably one or two, amino acid variations, including substitutions, insertions and deletions.

In another aspect of the invention there is provided a fusion polypeptide which comprises a first portion having the amino acid sequence of a polypeptide according to the invention as defined above and a second portion, attached to the N- or C-terminus of the first portion, which comprises a sequence of amino acid not naturally contiguous to the first portion. Such heterologous polypeptide fusions are also referred to herein as polypeptides of the invention.

The second polypeptide portion can be any sequence selected by those of skill in the art taking into account the intended purpose of the fusion. For example, the second portion may comprise a detectable tag such as a T7 tag, HA tag or a myc tag allowing identification of the polypeptide in a cell and/or its recovery. The second portion may also be a signal sequence directing expression of the polypeptide from a host cell in which the fusion is being expressed. This will be useful for the recombinant production of polypeptides of the invention.

The second portion may also comprise a molecular tag which influences the overall structure. A number of helix initiators which aid the formation of α-helices which comprise short peptide sequences are known in the art.

In a preferred embodiment the second polypeptide portion is a membrane translocation sequence, capable of directing a polypeptide through the membrane of a eukaryotic cell. Example of such polypeptides include the HSV-1 V22 protein (Elliot et al, 1997), the HIV Tat protein (for example residues 1–72, 37–72 or 48–60; Fawell et al, 1994) or a sequence that is derived from the *Drosophila melanogaster* antennapedia protein, e.g. the 16 amino acid peptide sequence: Arg-Gln-Ile-Lys-Ile-Trp-Phe-Gln-Asn-Arg-Arg-Met-Lys-Trp-Lys-Lys (SEQ ID NO:6).

A translocation peptide may be at the N-terminus or the C-terminus of the heterologous fusion.

In a further aspect, the invention provides a pharmaceutical composition comprising a polypeptide according to the invention together with a pharmaceutically acceptable carrier or diluent.

Polypeptides of the invention and compositions thereof may be used for a number of purposes. Such polypeptides are useful as research agents to investigate the interaction between E2F and DP-1, or the activation by E2F-1/DP-1 heterodimers of transcription. Peptides of the invention are useful in inducing cell cycle arrest and/or apoptosis in cells.

Thus in a preferred aspect the polypeptides of the invention may be used in a method of inducing apoptosis and/or cell cycle arrest in a cell, said method comprising introducing into the cell an effective amount of a polypeptide of the invention. The method may be practised in vitro or in vivo. Where it is practised in vivo the invention will find use in a method treatment of the human or animal body, particularly in methods of treating cancer or other proliferative diseases, including psoriasis and restenosis, e.g. caused by regrowth of vascular cells following angioplasty procedures.

In another aspect of the invention there is provided an expression vector comprising a promoter operably linked to a sequence encoding a polypeptide as defined above. The expression vector can be introduced into a host cell which is compatible with the origin of replication and/or the promoter of said vector.

DETAILED DESCRIPTION OF THE INVENTION

A (i)
E2F Protein

An E2F protein having a DNA binding site to which peptides of the invention may bind may be any member of the E2F family of proteins found in human or other mammalian or eukaryotic organisms. The human E2F proteins are described in the following references:

E2F-1: Helin et al, 1992, Cell, 70, 337–350;

E2F-2: Ivey-Hoile et al, 1993, Mol. Cell. Biol. 13, 7802–7812;

E2F-3: Lees et al, 1993, Mol. Cell. Biol. 13, 7813–7825;

E2F-4: Beijersbergen et al, 1994, Genes & Development, 8, 2680–2690;

E2F-5: Buck et al, 1995, Oncogene, 11, 31–38; and

E2F-6: Trimarchi et al, 1998, Proc. Natl. Acad. Sci. USA 95, 2850–2855.

Homologous polypeptides are found in other organisms, and the sequences of many of these are available on databases.

The E2F proteins bind to a consensus E2F binding site which contains the DNA sequence 5'-TTTCGCGC-3'. Examples of this binding site include:

B-myb: 5'-CTTGCGG-3'

Human E2F-1: 5'TTTCGCGG-3'

Human Cyclin E: 5'-TCTCCCGC-3' and 5'-TTTGCCGC-3'.

Polypeptides

Polypeptides of the invention comprise the sequences, fragments thereof and variants of said sequences and fragments as set out above, as well as heterologous fusions of said polypeptides.

The term "comprising" means "including" and allows for the presence of further amino acid sequences, or other chemical moieties, at the N- and/or C-termini, provided that the polypeptide as a whole retains the ability to bind to an E2F binding site. Binding to the E2F binding site by the use of a band shift assay method described herein (inhibition of E2F-1 binding to the B-myb E2F binding site), or other similar assays. Desirably, the $IC_{50}$ of a peptide of the invention in the abovementioned assay will be less than 100 $\mu M$, e.g. from 0.01 to 100 $\mu M$. More preferably, the $IC_{50}$ of a peptide of the invention will be less than 10 $\mu M$, e.g. from 0.01 to 10 $\mu M$. Peptides which do not have the ability to bind to an E2F binding site with sufficiently high affinity will have an $IC_{50}$ of greater than 500 $\mu M$, generally greater than 1000 $\mu M$.

It is preferred that peptides of the invention (including fragments of SEQ ID NOs 1–5 above and other sequences of the invention described herein), excluding any heterologous fusion sequence, are from 3 to 15, such as from 5 to 15, e.g. 5 to 8, 5 to 10, 8 to 15 or 8 to 11 amino acids in length.

The presence of a heterologous fusion sequence, which in itself has no activity in binding to the E2F DNA binding domain, will vary according to its intended function. Such functions include the ability to translocate across membranes, an epitope function to allow for purification or identification of the peptide, and the like. As a rough guide, the heterologous fusion sequence will be from 4 to 500, such as from 4 to 100 or 10 to 50, e.g from 10 to 30 amino acids in size.

A(ii). Variant Polypeptides

We have found that certain amino acid residues of polypeptides 1–5 above may be substituted without significant loss of the ability of the peptide to bind to the E2F DNA binding site. Thus, amino acids of these polypeptides may be substituted to provide variant polypeptides which form a further aspect of the invention, within the above-described ranges.

Substitutions may include conserved substitutions for example according to the following table, where amino acids on the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

Alternatively, any amino acid may be replaced by a small aliphatic amino acid, preferably glycine or alanine.

In addition, deletions and insertions may also be made. Insertions are preferably insertions of small aliphatic amino acids, such as glycine or alanine, although other insertions are not excluded.

Variant polypeptides may also modified in any of the ways described herein for polypeptides of the invention. This includes for example "reverse" C-terminal to N-terminal sequences, synthetic amino acids, modified side chains and labelling.

Where methods for the production and use of polypeptides of the invention are described, it will be understood that reference is also being made to variant polypeptides of the invention unless the context explicitly indicates otherwise.

In another aspect, a polypeptide of the invention may be provided in the form of molecules which contain multiple copies of the peptide (or mixtures of peptides of the invention). For example, the amino group of the side chain of lysine may be used as an attachment point for the carboxy terminus of an amino acid. Thus two amino acids may be joined to lysine via carbonyl linkages, leading to a branched structure which may in turn be branched one or more times. By way of example, four copies of a peptide of the invention may be joined to such a multiple antigen peptide (MAP), such as a MAP of the structure is $Pep_4$-$Lys_2$-Lys-X, where Pep is a peptide of the invention (optionally in the form of a heterologous fusion), Lys is lysine and X is a terminal group such as β-alanine which provides for joining of the MAP core to a solid support such as a resin for synthesis of the $Pep_4$-MAP peptide and which may be removed from the support once synthesis is complete.

Linear multimers of peptides of the invention may also be provided.

Other multiple peptide structures may be obtained using the MAP cores described in: Lu et al, 1991, Mol Immunol, 28, 623–30; Briand et al, 1992, J Immunol Methods, 156, 255–65; Ahlborg, 1995, J Immunol Methods, 179, 269–75.

A multimer of peptides of the present invention may be fused to a translocation peptide for directing it through the membrane of a eukaryotic cell, as discussed herein. A translocation peptide may be fused to an N-terminus or a C-terminus of the multimer, or it may be incorporated at an intermediate position within the multimer.

Where multimers of the invention are provided, they may comprise different peptides of the invention or be multimers of the same peptide.

In a more general aspect, a preferred polypeptide of the invention has the a structure of formula:

$X^{1a}$—$X^{Ar1}$—$X^{2a}$—$X^{Ar2a}$—$X^3$. (SEQ ID NO:7)

wherein:

$X^{1a}$ is an amino terminal or a sequence of from 1 to 4 amino acids;

$X^{Ar1}$ is an aromatic amino acid;

$X^{2a}$ is from two to four amino acids;

$X^{Ar2}$ is an aromatic amino acid; and $X^{3a}$ is a carboxy terminal or a sequence of from one to four amino acids.

It is preferred that:

$X^{1a}$ is an amino terminal or a sequence of from 1 to 4 amino acids;

$X^{Ar1}$ is F or W;

$X^{2a}$ is from two to four amino acids;

$X^{Ar2}$ is F or W; and $X^{3a}$ is a carboxy terminal or a sequence of from one to four amino acids.

It is more preferred that:

$X^{1a}$ is an amino terminal or a sequence of from 1 to 4 amino acids, each of which are selected from G, A, I, L, V, S, T, K or R;

$X^{Ar1}$ is F or W;

$X^{2a}$ is from two to four amino acids each of which are selected from G, A, I, L, V, S, T, K, R, H or F;

$X^{Ar2}$ is W; and $X^{3a}$ is a carboxy terminal or a sequence of from one to four amino acids each of which are selected from G, A, I, L, V, S, T, K, R, H, F or Y.

More particular polypeptides SEQ D NO:7 comprise, or more preferably consist of, the sequences:

WXXWXX (SEQ ID NO:8); where each X is independently any amino acid;

WXXWXF (SEQ ID NO:9); where each X is independently any amino acid selected from G, A, I, L, V, S, T, K, R, H, or F;

WXXWXFXXW (SEQ ID NO:10); where each X is independently any amino acid selected from G, A, I, L, V, S, T, K, R, H or F;

WXXWHF (SEQ ID NO:11); where each X is independently any amino acid selected from G, A, I, L, V, S, T, or R; and

WVRWHF (SEQ ID NO:2).

Further polypeptides of SEQ ID NO:7 comprise, or consist of, the sequences:

$X^{1b}X^{2b}FX^{4b}X^{5b}X^{6b}X^{7b}W$ (SEQ ID NO:12); where each $X^{1b-7b}$ is independently any amino acid;

$X^{1b}X^{2b}FX^{4b}X^{5b}X^{6b}X^{7b}W$ (SEQ ID NO:13); where each $X^{1b-7b}$ is independently any amino acid selected from G, A, I, L, V, S, T, K, R, H, F or Y;

$X^{1b}X^{2b}FRX^{5b}X^{6b}X^{7b}W$ (SEQ ID NO:14); where each $X^{1b, 2b}$ and each of $X^{5b-7b}$ is independently any amino acid selected from G, A, I, L, V, S, T, K, R, H, F or Y;

$X^{1b}X^{2b}FRX^{5b}X^{6b}X^{7b}W$ (SEQ ID NO:15); where $X^{1b}$ and $X^{2b}$ are independently selected from the group G, A, I, L, V, S, and T, and each of $X^{5b-7b}$ is independently selected from the group G, A, I, L, V, S, and T.

B. Production of Polypeptides

Except where specified to the contrary, the polypeptide sequences described herein are shown in the conventional 1-letter code and in the N-terminal to C-terminal orientation. The amino acid sequence of polypeptides of the invention may also be modified to include non-naturally-occurring amino acids or to increase the stability of the compound in vivo. When the compounds are produced by synthetic means, such amino acids may be introduced during production. The compound may also be modified following either synthetic or recombinant production.

Polypeptides of the invention may also be made synthetically using D-amino acids. In such cases, the amino acids will be linked in a reverse sequence in the C to N orientation. This is conventional in the art for producing such peptides.

A number of side-chain modifications for amino acids are known in the art and may be made to the side chains of polypeptides of the present invention. Such modifications include for example, modifications of amino groups by reductive alkylation by reaction with an aldehyde followed by reduction with $NaBH_4$, amidinaton with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a $C_{1-6}$alkyl ester The above examples of modifications to amino acids are not exhaustive. Those of skill in the art may modify amino acid side chains where desired using chemistry known per se in the art.

Polypeptides of the invention may be formulated in the form of a salt. Salts of polypeptides of the invention which may be conveniently used in therapy include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Salts also include physiologically acceptable acid addition salts, including the hydrochloride and acetate salts.

Polypeptides of the invention may be made synthetically or recombinantly, using techniques which are widely available in the art. Synthetic production generally involves step-wise addition of individual amino acid residues to a reaction vessel in which a polypeptide of a desired sequence is being made. Examples of recombinant techniques are described below.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

A polypeptide of the invention may be labelled with a revealing label. The revealing label may be any suitable label which allows the polypeptide to be detected. Suitable labels include radioisotopes, e.g. $^{125}I$, enzymes, antibodies, polynucleotides and linkers such as biotin. Labelled polypeptides of the invention may be used in diagnostic procedures such as immunoassays in order to determine the amount of a polypeptide of the invention in a sample.

A polypeptide or labelled polypeptide of the invention or fragment thereof may also be fixed to a solid phase, for example the surface of an immunoassay well or dipstick. Such labelled and/or immobilized polypeptides may be packaged into kits in a suitable container along with suitable reagents, controls, instructions and the like.

C. Heterologous Fusion Sequences

The heterologous fusion sequences mentioned above may be selected by those of skill in the art for a variety of purposes. For example the sequences may be selected to facilicate the recombinant production of polypeptides of the invention. Such sequences will include signal sequences such as the yeast α-factor leader sequence which direct a polypeptide out of a cell.

A further class of sequences are tags which allow the detection of the polypeptide or its recovery by, for example, affinity chromatography. Many such tags are available and include the T7 tag, the HA tag and a myc tag.

Another class of sequences which are preferred are membrane translocation sequences capable of directing the fusion polypeptide through the membrane of a eukaryotic cell. An example of such a sequence is that derived from the HIV tat protein, as illustrated in the accompanying examples.

Other membrane translocation sequences known in the art may be used in an analogous manner.

The membrane translocation sequence may be attached to the N- or C-terminus of the polypeptide of the invention.

Unless the context requires otherwise, reference below to polypeptides of the invention includes the fusion polypeptides described above.

D. Pharmaceutical Compositions

Polypeptides, including fusion polypeptides of the invention may be formulated into pharmaceutical compositions. The compositions comprise the polypeptide together with a pharmaceutically acceptable carrier or diluent. Pharmaceutically acceptable carriers or diluents include those used in formulations suitable for oral, topical, or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy)propyl]-N,N,N-triethylammonium (DOTMA), those comprising dioleoyl-phosphatidylethanolamine (DOPE), and those comprising 3β[N-(n',N'-dimethylaminoethane)-carbamoyl]cholesterol (DC-Chol).

Compositions may comprise any desired amount of a polypeptide of the invention. In part this will depend upon the intended formulation and its intended use. By way of general guidance the composition may comprise from about 1% to about 99%, for example from 10 to 90% of a polypeptide of the invention.

The composition may comprise a mixture of more than one, for example two or three, polypeptides of the invention.

Polypeptides of the invention may also be used in conjunction with a second agent capable of inhibiting cell proliferation, in order to provide a combined anti-proliferative effect. Thus the composition may also comprise other pharmaceutically active ingredients, in particular cytotoxic and/or cytostatic agents.

Alternatively, a polypeptide of the invention may be delivered to a patient in a separate composition from a cytotoxic or cytostatic agent but simultaneously or sequentially. "Sequentially" means that one of the polypeptide or the agent will be delivered first, and the other delivered within a period of time such that the enhanced effect of the two agents together is achieved in a target proliferating cell. Where one or both agents is delivered over a period of time, e.g. through intravenous infusion, the time period of administration of the agents may be sequential or overlapping.

When used in methods of treatment of the human or animal body, the polypeptide and the agent may be administered to a subject at the same site or at different sites.

Thus the invention provides a polypeptide of the invention and a cytotoxic or cytostatic agent for separate or simultaneous use in the treatment of proliferating cells, for example tumour cells, either in vitro or in vivo.

Where in vitro use is contemplated, this will include ex-vivo, e.g. in the treatment of bone marrow from a subject which may be reimplanted into the subject after treatment.

The invention further provides the use of a polypeptide of the invention for the manufacture of a medicament for the treatment of proliferating cells wherein said cells are also treated, separately or simultaneously, with a cytotoxic or cytostatic agent.

Numerous cytotoxic and/or cytostatic agents are known in the art (e.g. listed in The Merck Index, 12th Edition, 1996) and include:

alkaloids such as etoposide and other toposiomerase inhibitors, paclitaxel, vinblastine and vincristine; alkylating agents such as alkyl sulphonates (e.g. busulfan), aziridines, ethylenimines and methylmelomines (e.g. triethylenemelamine and triethylenephosphoramide), nitrogen mustards (e.g. cyclophosphamide, melphalan and uracil mustard, nitrosoureas and the like;

antibiotics and analogues such as actinomycins, anthramycin, doxorubicin, puromycin and the like;

antimetabolites such as folic acid analogues (e.g. methotrexate), purine analogues (e.g. 6-mercaptopurine and thioguanine) and pyrimidine analogues (e.g fluorouracil);

platinum complexes such as cisplatin; and other anti-neoplastic compounds including for example hydroxyurea.

In addition, the cytotoxic or cytostatic compound may be an immunomodulatory compound or hormonal analogue compound. Examples of the former include interferons α, β and γ and interleukins such as IL-2. Examples of the latter include antiandrogens, antiestrogens (e.g. tamoxifen), aromatase inhibitors, estrogen analogues, LHRH analogues (e.g. buserelin and the like.

Cytostatic compounds also include antimetastatic agents such as matrix metalloproteinase inhibitors such as batimastat.

E. Expression Vectors

In another aspect, the invention provides nucleic acids encoding polypeptides of the invention. Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Such vectors may be transformed into a suitable host cell to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which is can be included in response to heavy metals such as cadmium. Viral promoters include the SV40 large T antigen promoter, retroviral LTR promoters and adenovirus promoters. All these promoters are readily available in the art.

The vector may also be adapted to be used in vivo, for example in a method of therapy. Vectors suitable for use in therapy include adenoviral vectors, retroviral vectors and alphavirus vectors. Such vectors are adapted for use in therapy by a number of modifications, for example by making the vector replication defective. Reference may be made to, for example, WO95/14091 for a description of retroviral vectors and WO95/07994 for a description of alphavirus vectors. The disclosures of both references are hereby incorporated by reference.

Vectors for use in therapy will generally be administered in the form of packed viral particles containing the vector, the particles being delivered to the site of a tumour or other proliferating cells.

F. Assay Methods

The heterodimerization of DP proteins with E2F proteins during the progression of the cell cycle provides a target for the development of therapeutic agents capable of inhibiting uncontrolled cell proliferation, for example found in tumour cells.

A number of assay formats are described in the accompanying examples and in WO94/10307 and WO96/10425. The provision of the polypeptides of the invention provide positive control reagents for such assays which will be desirable in the design of high throughput screening assays for novel compounds which can exert a similar effect. The polypeptides of the invention further provide a basis for rational drug design of pharmaceutical compounds to target the DP/E2F heterodimer.

Polypeptides of the invention are also of use in investigating programmed cell death—apoptosis. While not wishing to be bound by any one theory, our findings indicate that inhibition of DNA binding by the DP-E2F heterodimer may result in apoptosis. The induction of apoptotic cell death is a particularly desirable aim of cancer therapy since this may avoid side-effects associated with cell lysis caused by some other therapeutic treatments.

The provision of model systems in which apoptosis is inducible allows the study of all aspects of this cell death mechanism and has applications in, for example oncology, and embryology.

Peptides in the present invention ray be used in screening assay to define mimotope peptides which behave in an analogous manner to peptides of the invert on but which do not have any sequence similarity. A number of assay methods to define peptide interaction with peptides are known. For example, WO86/00991 describes a method for determining mimotopes which comprises making panels of catamer preparations, for example octamers of amino acids, at which one or more of the positions is defined and the remaining positions are randomly made up of other amino acids, determining which catamer binds to a protein of interest and re-screening the protein of interest against a further panel based on the most reactive catamer in which one or more additional designated positions are systematically varied. This may be repeated throughout a number of cycles and used to build up a sequence of a mimotope of interest.

WO89/03430 describes screening methods which permit the preparation of specific mimotopes which mimic the immunological activity of a desired analyte. These mimotopes are identified by reacting a panel of individual peptides wherein said peptides are of systematically varying hydrophobicity, amphipathic characteristics and charge patterns, using an antibody against an antigen of interest. Thus in the present case antibodies against peptides of the invention may be employed and minotope peptides from such panels may be identified.

Mimotopes obtainable by the above and other methods available in the art form a further aspect of the present invention.

Peptides of the present invention may be used to develop mimetics. This might be desirable where the peptide is difficult or expensive to synthesise or where it is unsuitable for a particular method of administration, e.g. peptides may be unsuitable active agents for oral compositions as they may be quickly degraded by proteases in the alimentary canal. Mimetic design, synthesis and testing may be used to avoid randomly screening large numbers of peptides for a target property.

There are several steps commonly taken in the design of a mimetic from a peptide having a given target property. Firstly, the particular parts of the peptide that are critical and/or important in determining the target property are determined. In the case of a peptide, this can be done by systematically varying the amino acid residues in the peptide, e.g. by substituting each residue in turn. These parts or residues constituting the active region of the peptide are known as its "pharmacophore".

Once the pharmacophore has been found, its structure is modelled according to its physical properties, e.g. stereochemistry, bonding size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process. In a variant of this approach, the three-dimensional structure of the peptide and the DNA binding domain of E2F-1 are modelled in combination. This may be useful where the peptide and/or E2F-1 domain change conformation on biding, allowing the model to take account of this the design of the mimetic.

A template molecule is then selected onto which chemical groups which mimic the pharmacophore can be grafted. The template molecule and the chemical groups grafted on to it may conveniently be selected so that the mimetic is easy to synthesise, is likely to be pharmacologically acceptable, and does not degrade in vivo, while retaining the biological activity of the lead peptide. Alternatively, the pharmacophore can be used to form the basis of a search of a computer database of structures to identify a mimetic. The mimetic or mimetics found by any approach described herein can then be screened to see whether they have the target property or to what extent they exhibit it. Further optimisation and/or modification can then be carried out to arrive at one or more final mimetics for in vivo or clinical testing.

Mimetics obtainable by the above and other methods available in the art form a further aspect of the present invention.

G. Methods of Treatment

Polypeptides of the invention may also be used in methods of treating uncontrolled proliferation of cells. Conditions in which uncontrolled cell proliferation may be treated include psoriasis, restenosis and the treatment of tumours. Tumour cells include cells of solid tumours such as lung (including small cell lung), bowel (colon), breast, ovarian, prostate, stomach, liver, pancreatic and skin tumours, as well as leukaemias.

In general, the methods wall involve administering to a patient in need of treatment an effective amount of a polypeptide (or composition thereof) of the invention. Suitable routes of administration of compounds of the invention include oral or parenteral, and will depend in part upon the intended use and the discretion of the physician. Small peptides may be administered orally although parenteral administration may generally be more convenient in some circumstances.

The amount of polypeptides of the invention administered to a patient is ultimately at the discretion of the physician, taking account of the condition of the patient and the condition to be treated. Typical amounts of polypeptides of the invention required to achieve antagonism of the interaction of a action of an E2F protein will be in the region of from 0.1 $\mu$M to 10 mM, e.g. from 1 $\mu$M to 1 mM or more preferably from 1 $\mu$M to 100 $\mu$M in the body of a patient.

Doses may be administered continuously, e.g in the form of a drip, or at discrete intervals, e.g twice daily, daily, weekly or monthly. Doses may also be administered topically to achieve concentrations of active agent on the skin in the ranges described above.

Where a peptide of the invention is to be administered in conduction with a cytotoxic or cytostatic agent, the dose of said agent will be in accordance with manufacturers' instructions.

Peptides may be selectively directed to tumour cells by various mechanisms in order to enhance their effectiveness and to avoid effects on normal cells. Such mechanisms include coupling the peptides molecules to which specifically interact with receptors or antigens on target cells, such as VEGF receptors or CEA. Alternatively gene therapy vectors expression polypeptides of the invention may comprise an expression system whose promoter is selectively activated in tumour cells, such as promoters active in fetal liver cells.

In a further embodiment, the polypeptides of the invention may be incorporated into a stent which is introduced into the arteries of a patient during an angioplasty procedure. This is in order for the polypeptides of the invention to treat restenosis. The stent is a hollow metal tube, usually made of stainless steel and optionally coated with a polymeric material such as a plastic which is expanded during the procedure so as to be left in place in the artery to treat heart disease caused by arterial narrowing. A problem with this procedure is the occurrence of restenosis, i.e. the cardiovascular cells tend to grow back and further treatment is ultimately required. By coating the stent with a polypeptide of the invention, the polypeptide is delivered locally into the cardiovascular tissue and will prevent local regrowth of cells by antagonizing entry of the cells through the cell cycle.

Polypeptides of the invention may be either coated onto or incorporated into the stent by conventional means known per se in the art. For example, the polypeptides may be mixed with a pharmaceutically acceptable carrier compatible with the stent material and coated on or into the stent. Where incorporation into the stent is contemplated it is desirable that the stent comprises an open celled polymeric structure. Where the stent is in the form of a mesh, the polypeptides may be incorporated into a suitable delayed release carrier contained in the spaces between the mesh strands. Delayed release formulations are widely available for a number of different purposes in the art; these include formulations based on pharmaceutically acceptable polymers which dissolve slowly in the body following implantation.

A number of coronary stents have been approved for clinical use in the USA by the FDA. These include balloon expandable stents such as the Palmaz-Schatz stent made by Cordis Corporation (a division of Johnson & Johnson Interventional Systems) and the Gianturco-Roubin II (GR-II) stent made by Cook Cardiology (Bloomington, Ind., USA). Self-expanding stents are also used in the art, e.g. the Wallstent (Medinvent-Schneider, Switzerland) Generally these stents are made of a wire of around 0.1 mm (e.g. from 0.07 to 1.5 mm) diameter, are designed to expand to a diameter of 3–5 mm, and are around 10 to 20 mm in length.

Examples of stent coatings to which reference may be made for the provision of peptide coated stents of the invention include a heparin-coated Palmaz-Schatz stent (Serruys et al, Circulation, 1996, 93;412–422) and a platelet glycoprotein IIa/IIIa receptor antibody polymer-coated stent (Aggarwal et al, Circulation, 1996, 94;3311–3317).

For further guidance, those of skill in the art may also make reference to "Coronary Artery Stents", an ACC Expert Consensus Document (Pepine et al, J. Am. Coll. Cardiol., 1996, 28;782–794).

The following examples illustrate the invention.

EXAMPLES

Materials and Methods

Recombinant E2F

N-terminal fragments of human E2F1 (aa 64–301), E2F2 (aa 69–306), E2F3 (aa 128–356), E2F4 (aa 1–198), E2F5 (aa 42–233) were cloned into bacterial expression vector pET28b (Novagen) and were purified from BL21 DE3 cells by immobilised metal-affinity chromatography. A N-terminal fragment of DP1 (aa 85-249) was expressed as GST fusion protein and purified by glutathione-affinity chromatography.

Peptide Synthesis

Peptides were synthesised on a solid phase using a multiple peptides synthesizer employing Fmoc/t-butyl protecting groups. The Fmoc group was cleaved by 20% (v/v) piperidine in dimethylformamide and successive amino acids were added as N-hydroxybenzotriazole esters. The peptides were deprotected and cleaved from the resin by 93% trifluoroacetic acid, 3% ethaneditiol, 2% anisole, 2% water. Peptides were analyzed by high performance liquid chromatography. Tetravalent MAP4-D6-11 peptide was synthesized using a Fmoc4-Lys-βAla-Wang resin (Novabiochem) (Tam & Zavala (1989) J. Immunol. Meth. 124, 53–61).

Band Shift Assays

Purified E2F1 N1-His (64–301) and DP1 N2-GST (84–249) were incubated at 10 μg/ml in a buffer containing 10 mM HEPES, 100 nM KCl, 1 mM EDTA, 1 nM DTT, 33 mg/ml BSA and 0.1 μg of sonicated salmon sperm for 10 minutes on ice. $^{32}$P-labelled probe was added and the reaction mixture was incubated at room temperature for 20 minutes. Probes were labelled by filling-in 5' overhanging ends of 4–7 bases. Samples were run on 4% non denaturing polyacrylamide gel in 0.5% TBE at 4° C. Gels were exposed to X-ray films. Nuclear extract (3 μg) was incubated in 17 μl buffer containing 0.3 M NaCl, 0.4 M Tris pH 7.9, 100 mM EDTA, 0.4 M DTT, 13% glycerol, 1 μg of sonicated salmon sperm on ice. The samples were then incubated for 10 minutes at 30° C. and cooled on ice. $^{32}$P-labelled probe was added, the reaction mixtures were incubated for another 10 minutes at 30° C. and then cooled on ice.

Oligonucleotide Probes

B-myb: (5'-CGACGCGCTTGGCGGGAGATAGAA AAGTGC) (SEQ ID NO:16)

NF-Y: 5'-ATTTTTCTGATTTGGTTAA (SEQ ID NO:17)

Spl: 5'-ATGGGGCGGAGA (SEQ ID NO:18)

ATF: 5'-CGCCTTGAATGACGTCAAGGCCSCGA (SEQ ID NO:19)

Introduction of Peptides into Mammalian Cells

HeLa cells were grown in Dulbecco's Modified Eagle's Medium (DMEM) supplemented with fetal calf serum (FCS) and HL60 cells in RPMI 1640 supplemented with 10% FCS. Cells were treated with peptides in culture medium and incubated overnight before harvesting.

Isolation of Genomic DNA and Nuclease-laddering Assay

Treated cells were collected, washed with PBS, resuspended in lysis buffer (50 mM Tris pH 7.9, 100 mM EDTA, pH 8, 100 mM NaCl, 1% SDS) and 500 μg/ml proteinase K and incubated at 55° C. for 18 h. Cells were then incubated with 300 μg/ml for 1 hour at 37° C., genomic DNA was purified and examined by agarose gel electrophoresis.

Nuclear Extract Preparation

Cells were washed twice with cold PBS and scraped using a policeman. Cells were collected and centrifuged at 4° C. for 3 minutes at 1500 rpm. The pellet was resuspended in a buffer containing 20 mM Hepes pH7.8, 450 mM NaCl, 25% glycerol, 0.2 mM EDTA, 0.5 mM DTT, 0.5 mM PMSF, freshly added before use. Cells were frozen and thawed at 30° C. three times and centrifuged for 5 min at 4° C. The supernatant was collected, aliquoted and stored at −80° C.

Results

Five peptides were identified which bind to the DNA binding site of E2F-1. Competition ELISA experiments demonstrated that all five bind to identical or overlapping regions of E2F-1.

TABLE 1

Selected peptides against E2F1

| | |
|---|---|
| SEQ ID NO: 1 | FWLRFT |
| SEQ ID NO: 2 | WVRWHF |
| SEQ ID NO: 3 | WHFIFW |
| SEQ ID NO: 4 | IWLSGLSRGVWVSFP |
| SEQ ID NO: 5 | GSRILTFRSGSWYAS |

Inhibition of DNA-binding of Recombinant E2F

The inhibitory potential of the peptides on E2F function was analysed in band shift assays with recombinant E2F1 and DP1. Inhibition of DNA binding was observed for all 3 tested synthetic peptides SEQ ID NO:2, SEQ ID NO:4 and SEQ ID NO:5 using a B-myb E2F-binding site as probe. The $IC_{50}$ concentrations for the 3 peptides were in the range of 50–100 μM. Inhibition to various extends was also observed using recombinant fragments of E2F2, E2F3, E2F4, E2F5, respectively. Approximately 100-fold lower IC50 values were found with a branched molecule consisting of 4 copies of SEQ ID NO:2 linked by MAP (multiple antigen peptide).

Alanine-scanning of SEQ ID NO:2

The peptide SEQ ID NO:2 (WVRWHF) was further analysed in alanine-scanning experiments for the identification of important amino acids substituting single amino acids by alanine. This experiment showed that the amino acids Trp-1, Trp-4 are essential for complete inhibition and that Phe-6 also contributed to the inhibition. No effects were observed upon substitution of positions 2, 3, or 5.

TABLE 2

SEQ ID NO: 2 Alanine-scanning

| peptide | | sequence | inhibition |
|---|---|---|---|
| SEQ ID NO: 2 | | WVRWHF | 0 |
| SEQ2-A1 | (SEQ ID NO: 20) | AVRWHF | – |
| SEQ2-A2 | (SEQ ID NO: 21) | WARWHF | 0 |
| SEQ2-A3 | (SEQ ID NO: 22) | WVAWHF | 0 |
| SEQ2-A4 | (SEQ ID NO: 23) | WVRAHF | – |
| SEQ2-A5 | (SEQ ID NO: 24) | WVRWAF | 0 |
| SEQ2-A6 | (SEQ ID NO: 25) | WVRWHA | (+) |

Mutational Analysis of SEQ ID NO:5

A deletion analysis of the SEQ ID NO:5 peptide identified a core-region consisting of amino acids 3–13 (SEQ5-7). However, this region exhibited only approximately 50% of the inhibitory activity of SEQ ID NO:5. Shorter peptides were completely inactive.

The SEQ ID NO:5 peptide was further analysed by alanine scanning which showed that the amino acids Phe-7 and Trp-12 are essential for complete inhibition, and that Arg-8 also contributes to the inhibition. No effects were observed upon mutation Arg-3 or Tyr-13 to alanine. The other positions were not analysed by alanine substitution.

TABLE 3

SEQ ID NO: 5 Mutational analysis

| peptide | | sequences | inhibition |
|---|---|---|---|
| SEQ ID NO: 5 | | GSRILTFRSGSWYAS | ++ |
| SEQ5-1 (1–9) | (SEQ ID NO: 26) | GSRILTFRS | – |
| SEQ5-2 (4–12) | (SEQ ID NO: 27) | ILTFRSGSW | – |
| SEQ5-3 (7–15) | (SEQ ID NO: 28) | FRGSWAS | – |
| SEQ5-4 (5–15) | (SEQ ID NO: 29) | LTFRSGSWYAS | +/– |
| SEQ5-5 (3–15) | (SEQ ID NO: 30) | RILTFRSGSWYAS | ++ |
| SEQ5-6 (3–11) | (SEQ ID NO: 31) | RILTFRSGS | – |

TABLE 3-continued

SEQ ID NO: 5 Mutational analysis

| peptide | | sequences | inhibition |
|---|---|---|---|
| SEQ5-7 (3–13) | (SEQ ID NO: 32) | RILTFRSGSWY | ++ |
| SEQ5-8 (2–13) | (SEQ ID NO: 33) | SRILTFRSGSWY | ++ |

TABLE 4

SEQ ID NO: 5 Alanine scanning

| peptide | | sequences | inhibition |
|---|---|---|---|
| SEQ ID NO: 5 | | GSRILTFRSGSWYAS | ++ |
| SEQ5-A3 | (SEQ ID NO: 34) | GSAILTFRSGSWYAS | ++ |
| SEQ5-A7 | (SEQ ID NO: 35) | GSRILTARSGSWYAS | – |
| SEQ5-A8 | (SEQ ID NO: 36) | GSRILTFASGSWYAS | (+) |
| SEQ5-A12 | (SEQ ID NO: 37) | GSRILTFRSGSAYAS | — |
| SEQ5-A13 | (SEQ ID NO: 38) | GSRILTFRSGSWAAS | ++ |

Inhibition of E2F-DNA-binding in Nuclear Extracts

We investigated the effects of peptides SEQ ID NO:2 and SEQ ID NO:5 on DNA-binding of E2F in nuclear extracts prepared from various cell lines. With extracts from F9 embryonal carcinoma cells and HeLa cells a specific inhibition with SEQ ID NO:5 was observed at an IC50 of approximately 100 µM and with MP-4-SEQ ID NO:5 at an IC50 of approximately 10 µM. No inhibition was observed in band shift assay experiments with unrelated binding sites (ATF, Sp1) No inhibition, was observed for peptide SEQ ID NO:2 up to 500 µM. However, using MAP4-SEQ ID NO:2 an inhibition of E2F-DNA binding was found at around 10 µM–30 µM using F9 and HeLa nuclear extracts. Again, no inhibition was observed with an ATF control oligo. Using stable transfected 3T3 cells overexpressing E2F1, E2F2, E2F3, E2F4 or E2F5, respectively, we found inhibition of DNA-binding of all five members with peptides MAP4-SEQ ID NO:2 and MAP4-SEQ ID NO:5 at IC50 values of approximately 30 µM. No inhibition was observed under the same condition using unrelated binding sites like NFY.

Inhibition of Cell Cycle Progression and Induction of Apoptosis

The peptides were tested in further experiments for their effect on cell cycle progression and cell viability. For this purpose, the peptides were conjugated at their C-terminus to a cell penetrating HIV-Tat derived peptide (aa 48–60) (Fawell et al. (1994) Proc. Natl. Acad. Sci. USA 91, 664–668).

HeLa, 3T3, W138 cells were treated with varying concentration of MAP-4-SEQ ID NO:2-TAT and a control peptide MAP-4-SEQ ID NO:39-TAT wherein SEQ ID NO:39 is SEQ ID NO:2 but containing 2 alanine substitutions at positions 1 and 4, i.e. AVRAHF (SEQ ID NO:39) DNA replication was analysed by BrdU incorporation after 24 hours. A specific inhibition of cell proliferation by MAP-4-SEQ ID NO:2-TAT was observed with an IC50 of approximately 3–10 µM. Inhibition of cell proliferation was observed with HL60 cells treated with peptide MAP-4-SEQ ID NO:2-TAT at concentrations between 1–5 µM, while no inhibitory effects were observed with the control peptide MAP-4-SEQ ID NO:39-TAT at the same concentration. These results are presented in FIG. 1.

Effects became visible after 5–24 hours defending on the concentration of the peptide. In a similar experiment specific inhibition of cell growth was also observed using MAP-4-SEQ ID NO:5-TAT at concentration between 1–5 µM while no effects were observed with the control peptide MAP-4-SEQ ID NO:40-TAT (wherein SEQ ID NO:40 is SEQ ID NO:5 but containing alanine at positions 7 and 12, i.e. GSRILTARSGSAYAS (SEQ ID NO:40)) at the same concentration. HL60 cells treated with MAP-4-SEQ ID NO:2-TAT showed chromatin condensation and nuclear fragmentation after staining cells with Heochst 33342 propidium iodide, which are hallmarks of apoptosis. In agreement with these observations, we found internucleosomal DNA cleavage in MAP-4-SEQ ID NO:2-TAT treated HL60 cells ("DNA laddering"). No effects were observed in both experiments with the MAP-4-SEQ ID NO:39-TAT control peptide.

Inhibition of Transcription from the CycA Promoter

Inhibition of transcription was observed in HeLa cells transiently transfected with CycA-Luciferase construct and treated with MAP-4-SEQ ID NO:2-TAT. This finding is in agreement with the anti-repressor function of E2F in the CycA promoter, (Liu et al, Oncogene (1998), 16, 2957–2963). No effect was observed with the control peptide MAP-4-SEQ ID NO:39-TAT or with the SV-40 promoter, indicating that the effect of MAP-4-SEQ ID NO:2-TAT is specific for E2F.

Inhibition of Tumour Cell Growth

Four tumor cell lines U2OS (osteosarcoma), C33A (cervical carcinoma), HeLa (cervical carcinoma) and E2F4/ras (derived from primary rat embryo fibroblasts) were treated with the branched peptide MAP-4-SEQ ID NO:2-TAT or mutant control peptide MAP-4-SEQ ID NO:39-TAT for 24 hrs. Cell proliferation was measured using the BrDU proliferation assay from Boehringer Mannheim (Cat No. 1 647 229). The results are shown in FIGS. 2A–D.

The peptide MAP-4-SEQ ID NO:2-TAT inhibited proliferation of all four cell lines. This effect was dose-dependent and was not displayed by the control mutant peptide. The effects on the E2F4/ras line are of particular significance since this cell line grows very rapidly in culture and forms aggressive tumors in nude mice (Beljersbergen et al. 1994 Genes Dev. 8 2680–2690) and E2F has been observed to be over-expressed in a variety of tumor cell lines (Saito et al. 1995 Genomics 25 130–138; DeMuth et al. 1998 Am. J. Cell. Mol. Biol. 19 18–24; Rodriguez-Puebla et al. 1998 Oncogene 17 2551–2558).

Thus peptides of the invention may be used to inhibit cell cycle progression and/or induce apoptosis in cells in which an E2F family member, such as E2F-1, E2F-2, E2F-3, E2F-4 or E2F-5, is over-expressed.

SEQUENCE LISTING

<160> NUMBER OF SEQ ID NOS: 40

<210> SEQ ID NO 1
<211> LENGTH: 6

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Trp Leu Arg Phe Thr
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Val Arg Trp His Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp His Phe Ile Phe Trp
 1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Trp Leu Ser Gly Leu Ser Arg Gly Val Trp Val Ser Phe Pro
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ser Arg Ile Leu Thr Phe Arg Ser Gly Ser Trp Tyr Ala Ser
 1               5                  10                  15

<210> SEQ ID NO 6
<211> LENGTH: 16
<212> TYPE: PRT
<213> ORGANISM: Drosophila melanogaster

<400> SEQUENCE: 6

Arg Gln Ile Lys Ile Trp Phe Gln Asn Arg Arg Met Lys Trp Lys Lys
 1               5                  10                  15
```

```
<210> SEQ ID NO 7
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: In Claims 1 & 2, Xaa is an amino terminal or a
      sequence of from 1 to 4 amino acids
<221> NAME/KEY: SITE
<222> LOCATION: (1)
<223> OTHER INFORMATION: In Claim 3, Xaa is an amino terminal or a
      sequence of from 1 to 4 amino acids each of which are selected
      from Gly, Ala, Ile, Leu, Val, Ser, Thr, Lys, or Arg
<221> NAME/KEY: SITE
<222> LOCATION: (2)
<223> OTHER INFORMATION: In Claim 1, Xaa is an aromatic amino acid
<221> NAME/KEY: SITE
<222> LOCATION: (2)
<223> OTHER INFORMATION: In Claims 2 and 3, Xaa is Phe or Trp
<221> NAME/KEY: SITE
<222> LOCATION: (3)
<223> OTHER INFORMATION: In Claims 1 & 2, Xaa is from two to four amino
      acids
<221> NAME/KEY: SITE
<222> LOCATION: (3)
<223> OTHER INFORMATION: In Claim 3, Xaa is from two to four amino acids
      each of which are selected from Gly, Ala, Ile, Leu, Val, Ser, Thr,
      Lys, Arg, His or Phe
<221> NAME/KEY: SITE
<222> LOCATION: (4)
<223> OTHER INFORMATION: In Claim 1, Xaa is an aromatic amino acid
<221> NAME/KEY: SITE
<222> LOCATION: (4)
<223> OTHER INFORMATION: In Claim 2, Xaa is Phe or Trp
<221> NAME/KEY: SITE
<222> LOCATION: (4)
<223> OTHER INFORMATION: In Claim 3, Xaa is Trp
<221> NAME/KEY: SITE
<222> LOCATION: (5)
<223> OTHER INFORMATION: In Claims 1 & 2, Xaa is a carboxy terminal or a
      sequence of from one to four amino acids
<221> NAME/KEY: SITE
<222> LOCATION: (5)
<223> OTHER INFORMATION: In Claim 3, Xaa is a carboxy terminal or a
      sequence of from one to four amino acids each of which are
      selected from Gly, Ala, Ile, Leu, Val, Ser, Thr, Lys, Arg, His,
      Phe or Tyr
<223> OTHER INFORMATION: Description of Artificial Sequence: Synthetic
      peptide

<400> SEQUENCE: 7

Xaa Xaa Xaa Xaa Xaa
  1               5

<210> SEQ ID NO 8
<211> LENGTH: 6
<212> TYPE: PRT
<213> ORGANISM: Artificial Sequence
<220> FEATURE:
<221> NAME/KEY: SITE
<222> LOCATION: (2)..(3), (5)..(6)
<223> OTHER INFORMATION: Each Xaa is independently any amino acid
<223> OTHER INFORMATION: Description of Artificial Sequence: Synthetic
      peptide

<400> SEQUENCE: 8

Trp Xaa Xaa Trp Xaa Xaa
  1               5

<210> SEQ ID NO 9
<211> LENGTH: 6
<212> TYPE: PRT
<213> ORGANISM: Artificial Sequence
<220> FEATURE:
```

```
<221> NAME/KEY: SITE
<222> LOCATION: (2)..(3), (5)
<223> OTHER INFORMATION: Each Xaa is independently any amino acid
      selected from Gly, Ala, Ile, Leu, Val, Ser, Thr, Lys, Arg,
      His, or Phe
<223> OTHER INFORMATION: Description of Artificial Sequence: Synthetic
      peptide

<400> SEQUENCE: 9

Trp Xaa Xaa Trp Xaa Phe
 1               5

<210> SEQ ID NO 10
<211> LENGTH: 9
<212> TYPE: PRT
<213> ORGANISM: Artificial Sequence
<220> FEATURE:
<221> NAME/KEY: SITE
<222> LOCATION: (2)..(3), (5), (7)..(8)
<223> OTHER INFORMATION: Each Xaa is independently any amino acid
      selected from Gly, Ala, Ile, Leu, Val, Ser, Thr, Lys, Arg,
      His, or Phe
<223> OTHER INFORMATION: Description of Artificial Sequence: Synthetic
      peptide

<400> SEQUENCE: 10

Trp Xaa Xaa Trp Xaa Phe Xaa Xaa Trp
 1               5

<210> SEQ ID NO 11
<211> LENGTH: 6
<212> TYPE: PRT
<213> ORGANISM: Artificial Sequence
<220> FEATURE:
<221> NAME/KEY: SITE
<222> LOCATION: (2)..(3)
<223> OTHER INFORMATION: Each Xaa is independently any amino acid
      selected from Gly, Ala, Ile, Leu, Val, Ser, Thr, or Arg
<223> OTHER INFORMATION: Description of Artificial Sequence: Synthetic
      peptide

<400> SEQUENCE: 11

Trp Xaa Xaa Trp His Phe
 1               5

<210> SEQ ID NO 12
<211> LENGTH: 8
<212> TYPE: PRT
<213> ORGANISM: Artificial Sequence
<220> FEATURE:
<221> NAME/KEY: SITE
<222> LOCATION: (1)..(2), (4)..(7)
<223> OTHER INFORMATION: Each Xaa is independently any amino acid
<223> OTHER INFORMATION: Description of Artificial Sequence: Synthetic
      peptide

<400> SEQUENCE: 12

Xaa Xaa Phe Xaa Xaa Xaa Xaa Trp
 1               5

<210> SEQ ID NO 13
<211> LENGTH: 8
<212> TYPE: PRT
<213> ORGANISM: Artificial Sequence
<220> FEATURE:
<221> NAME/KEY: SITE
<222> LOCATION: (1)..(2), (4)..(7)
<223> OTHER INFORMATION: Each Xaa is independently any amino acid
      selected from Gly, Ala, Ile, Leu, Val, Ser, Thr, Lys, Arg,
      His, Phe, or Tyr
<223> OTHER INFORMATION: Description of Artificial Sequence: Synthetic
```

```
        peptide

<400> SEQUENCE: 13

Xaa Xaa Phe Xaa Xaa Xaa Xaa Trp
 1               5

<210> SEQ ID NO 14
<211> LENGTH: 8
<212> TYPE: PRT
<213> ORGANISM: Artificial Sequence
<220> FEATURE:
<221> NAME/KEY: SITE
<222> LOCATION: (1)..(2)
<223> OTHER INFORMATION: Each Xaa is independently any amino acid
      selected from Gly, Ala, Ile, Leu, Val, Ser, Thr, Lys, Arg,
      His, Phe, or Tyr
<221> NAME/KEY: SITE
<222> LOCATION: (5)
<223> OTHER INFORMATION: Xaa is independently any amino acid selected
      from Gly, Ala, Ile, Leu, Val, Ser, Thr, Lys, Arg, His, Phe, or Tyr
<221> NAME/KEY: SITE
<222> LOCATION: (6)
<223> OTHER INFORMATION: Xaa is independently any amino acid selected
      from Gly, Ala, Ile, Leu, Val, Ser, Thr, Lys, Arg, His, Phe, or Tyr
<221> NAME/KEY: SITE
<222> LOCATION: (7)
<223> OTHER INFORMATION: Xaa is independently any amino acid selected
      from Gly, Ala, Ile, Leu, Val, Ser, Thr, Lys, Arg, His, Phe, or Tyr
<223> OTHER INFORMATION: Description of Artificial Sequence: Synthetic
      peptide

<400> SEQUENCE: 14

Xaa Xaa Phe Arg Xaa Xaa Xaa Trp
 1               5

<210> SEQ ID NO 15
<211> LENGTH: 8
<212> TYPE: PRT
<213> ORGANISM: Artificial Sequence
<220> FEATURE:
<221> NAME/KEY: SITE
<222> LOCATION: (1)
<223> OTHER INFORMATION: Xaa is independently selected from the group
      Gly, Ala, Ile, Leu, Val, Ser, and Thr
<221> NAME/KEY: SITE
<222> LOCATION: (2)
<223> OTHER INFORMATION: Xaa is independently selected from the group
      Gly, Ala, Ile, Leu, Val, Ser, and Thr
<221> NAME/KEY: SITE
<222> LOCATION: (5)
<223> OTHER INFORMATION: Xaa is independently selected from the group
      Gly, Ala, Ile, Leu, Val, Ser, and Thr
<221> NAME/KEY: SITE
<222> LOCATION: (6)
<223> OTHER INFORMATION: Xaa is independently selected from the group
      Gly, Ala, Ile, Leu, Val, Ser, and Thr
<221> NAME/KEY: SITE
<222> LOCATION: (7)
<223> OTHER INFORMATION: Xaa is independently selected from the group
      Gly, Ala, Ile, Leu, Val, Ser, and Thr
<223> OTHER INFORMATION: Description of Artificial Sequence: Synthetic
      peptide

<400> SEQUENCE: 15

Xaa Xaa Phe Arg Xaa Xaa Xaa Trp
 1               5

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
```

```
                             Oligonucleotide probe

<400> SEQUENCE: 16
cgacgcgctt ggcgggagat agaaaagtgc                                             30

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 17
atttttctga tttggttaa                                                         19

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 18
atggggcgga ga                                                                12

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 19
cgccttgaat gacgtcaagg ccgcga                                                 26

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Val Arg Trp His Phe
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Ala Arg Trp His Phe
  1               5

<210> SEQ ID NO 22
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 22

Trp Val Ala Trp His Phe
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Val Arg Ala His Phe
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Val Arg Trp Ala Phe
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Val Arg Trp His Ala
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Arg Ile Leu Thr Phe Arg Ser
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Leu Thr Phe Arg Ser Gly Ser Trp
 1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Arg Gly Ser Trp Ala Ser
  1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Thr Phe Arg Ser Gly Ser Trp Tyr Ala Ser
  1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ile Leu Thr Phe Arg Ser Gly Ser Trp Tyr Ala Ser
  1               5                  10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ile Leu Thr Phe Arg Ser Gly Ser
  1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ile Leu Thr Phe Arg Ser Gly Ser Trp Tyr
  1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

```
Ser Arg Ile Leu Thr Phe Arg Ser Gly Ser Trp Tyr
  1               5                  10
```

```
<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser Ala Ile Leu Thr Phe Arg Ser Gly Ser Trp Tyr Ala Ser
  1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ser Arg Ile Leu Thr Ala Arg Ser Gly Ser Trp Tyr Ala Ser
  1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Arg Ile Leu Thr Phe Ala Ser Gly Ser Trp Tyr Ala Ser
  1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Arg Ile Leu Thr Phe Arg Ser Gly Ser Ala Tyr Ala Ser
  1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Arg Ile Leu Thr Phe Arg Ser Gly Ser Trp Ala Ala Ser
  1               5                  10                  15

<210> SEQ ID NO 39
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 39

Ala Val Arg Ala His Phe
 1               5

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ser Arg Ile Leu Thr Ala Arg Ser Gly Ser Ala Tyr Ala Ser
 1               5                  10                  15
```

What is claimed is:

1. An isolated polypeptide of up to 15 amino acids in length which includes the sequence WXXWXF (SEQ ID NO:9) where each X is independently any amino acid selected from G, A, I, L, V, S, T, K, R or H; said polypeptide inhibiting the binding of an E2F protein to an E2F DNA binding site with an in vitro IC50 of less than 100 $\mu$M.

2. The polypeptide of claim 1 wherein said sequence is WXXWHF (SEQ ID NO:11); where each X is independently any amino acid selected from G, A, I, L, V, S, T, or R.

3. The polypeptide of claim 2 wherein said sequence is WVRWHF (SEQ ID NO:2).

4. An isolated polypeptide WVRWHF (SEQ ID NO:2) or a variant thereof, which variant comprises from one or two amino acid substitutions, or three conservative amino acid substitutions, and which is capable of binding to an E2F DNA-binding site.

5. A polypeptide which comprises a first portion which has the amino acid sequence of a polypeptide of up to 15 amino acids in length which includes the sequence WXXWXF (SEQ ID NO:9) where each X is independently any amino acid selected from G, A, I, L, V, S, T, K, R, H or F, said polypeptide further comprising a second portion, attached to the N- or C-terminus of the first portion, which comprises a sequence of amino acids not naturally contiguous to the first portion, said second portion comprising a membrane translocation sequence.

6. A polypeptide which comprises a first portion which has the amino acid sequence of a polypeptide of up to 15 amino acids in length which includes the sequence WXXWXF (SEQ ID NO:9) where each X is independently any amino acid selected from G, A, I, L, V, S, T, K, R, H or F, and said polypeptide inhibits the binding of an E2F protein to an E2F binding site with an in vitro IC50 of less than 100 $\mu$M, said polypeptide further comprising a second portion, attached to the N- or C- terminus of the first portion, which comprises a sequence of amino acids not naturally contiguous to the first portion, said second portion comprising a membrane translocation sequence.

7. A composition comprising the polypeptide of claim 1 in association with a carrier or diluent.

8. A composition comprising the polypeptide of claim 3 in association with a carrier or diluent.

9. A multiple antigen peptide of the structure Pep$_4$-Lys$_2$-Lys-X, where Pep is a polypeptide of up to 15 amino acids in length which includes the sequence WXXWXF (SEQ ID NO:9) where each X is independently any amino acid selected from G, A, I, L, V, S, T, K, R, H or F, Lys is lysine and X is a terminal group.

10. A multiple antigen peptide of the structure Pep$_4$-Lys$_2$-Lys-X, where Pep is a polypeptide of up to 15 amino acids in length which includes the sequence WVRWHF (SEQ ID NO:2) or a fragment thereof capable of binding to an E2F DNA-binding site, Lys is lysine and X is a terminal group.

11. An in vitro method of inhibiting the growth of a eukaryotic cell which comprises bringing the cell into contact with the polypeptide of claim 1 under conditions to provide for apoptosis.

12. An in vitro method of inhibiting the growth of a eukaryotic cell which comprises bringing the cell into contact with the polypeptide of claim 3 under conditions to provide for apoptosis.

13. An in vitro method of inhibiting the growth of a eukaryotic cell which comprises bringing the cell into contact with the polypeptide of claim 5 under conditions to provide for apoptosis.

14. An in vitro method of inhibiting the growth of a eukaryotic cell which comprises bringing the cell into contact with the polypeptide of claim 6 under conditions to provide for apoptosis.

15. An in vitro method of inhibiting the growth of a eukaryotic cell which comprises bringing the cell into contact with the polypeptide of claim 9 under conditions to provide for apoptosis.

16. An in vitro method of inhibiting the growth of a eukaryotic cell which comprises bringing the cell into contact with the polypeptide of claim 10 under conditions to provide for apoptosis.

* * * * *